United States Patent [19]

Magee, Jr. et al.

[11] 4,359,431

[45] Nov. 16, 1982

[54] PREPARATION OF ARYLPHOSPHINIC ACIDS

[75] Inventors: Walter L. Magee, Jr., Danbury, Conn.; Arthur C. Bayer, Yorktown Heights, N.Y.

[73] Assignee: Stauffer Chemical Company, Westport, Conn.

[21] Appl. No.: 259,880

[22] Filed: May 4, 1981

[51] Int. Cl.³ .............................................. C07F 9/48
[52] U.S. Cl. ............................................ 260/502.4 R
[58] Field of Search ................................. 260/502.4 R

[56] References Cited

U.S. PATENT DOCUMENTS

| 2,137,792 | 11/1938 | Woodstock | 260/504.2 R |
| 2,594,454 | 4/1952 | Kosolapoff | 260/502.4 R |
| 2,632,018 | 3/1953 | Kosolapoff | 260/502.4 R |
| 3,903,208 | 9/1975 | Hofer et al. | 260/502.4 R |
| 3,974,217 | 8/1976 | Miles | 260/502.4 R |

OTHER PUBLICATIONS

"Organic Synthesis", 31, pp. 88–90, (1951).
Kosolapoff, "Organophosphorus Compounds", 1950, pp. 43–46 and 128.
Van Wazer, "Phosphorus and Its Compounds", vol. 1, pp. 371, 379 and 380, (1958).

Primary Examiner—Joseph E. Evans

[57] ABSTRACT

Arylphosphinic acids are prepared by reacting an aromatic compound with phosphorus trichloride in the presence of aluminum chloride to form an aluminum/phosphorus complex and then hydrolyzing the complex with aqueous phosphoric acid to form the arylphosphinic acid as an insoluble phase and a soluble aluminum salt. The arylphosphinic acid and aluminum salt are then easily separated.

6 Claims, No Drawings

PREPARATION OF ARYLPHOSPHINIC ACIDS

BACKGROUND OF THE INVENTION

The present invention relates to an improved process for the preparation of arylphosphinic acids. More particularly, the present invention relates to a process for preparing arylphosphinic acids by an aluminum chloride catalyzed reaction of an aromatic compound with phosphorus trichloride in which the prior art difficulties associated with separating the product from aluminum chloride complexes are effectively solved.

Arylphosphinic acids are compounds which are useful as catalysts and stabilizers in nylon synthesis and are also useful as intermediates in the production of a wide variety of useful compositions, such as pesticides, fuel and oil additives and the like.

One of the best known methods for preparing these compounds involves the reaction of an aromatic compound with phosphorus trichloride in the presence of aluminum trichloride to produce an aryl phosphonous dichloride, which is then hydrolyzed to produce the acid. Unfortunately, however, the aluminum chloride forms certain complexes during the process, which makes recovery of the final product difficult.

A method suggested by the prior art for circumventing the problems presented by the aluminum chloride complexes involves the addition of phosphorus oxychloride to the reaction mixture to form an aluminum chloride-phosphorus oxychloride complex, which settles from the reaction mixture, thereby facilitating recovery of the aryl phosphonous dichloride product. While this method is helpful, it is less than desirable because large amounts of phosphorus oxychloride are required and the remaining aluminum chloride-phosphorus oxychloride precipitate is a reactive waste product which can be difficult to dispose of. In addition, not all of the aluminum complex is removed, and the small amount remaining can lead to the formation of an emulsion during a subsequent reaction of the aryl phosphonous dichloride with water, which further complicates the process.

U.S. Pat. No. 3,974,217 teaches the preparation of alkoxy and alkylthio substituted phenyl phosphonous dichlorides by reacting an appropriate substituted aromatic compound with phosphorus trichloride in the presence of stannic chloride or titanium tetrachloride. It would appear, however, that this method would be less than successful with compounds not having the activating alkoxy or alkylthio substituents, since the catalysts used are less effective Friedel-Crafts catalysts.

A need therefore exists for a method by which arylphosphinic acids can be prepared from appropriate aromatic compounds and phosphorus trichloride using aluminum chloride as catalyst without encountering the prior art difficulties occasioned by the formation of aluminum chloride complexes.

SUMMARY OF THE INVENTION

It has now been found that arylphosphinic acids can be prepared from appropriate aromatic compounds and phosphorus trichloride, using aluminum chloride catalyst, without encountering the prior art difficulties occasioned by the presence of aluminum chloride complexes by adding the initial reaction product to an aqueous phosphoric acid solution to convert the aluminum to a soluble aluminum salt and to form the arylphosphinic acid as an insoluble phase.

DETAILED DESCRIPTION OF THE INVENTION

In accordance with the present invention there is provided a process for the preparation of arylphosphinic acids comprising reacting an aromatic compound susceptible to electrophilic ring substitution with phosphorus trichloride in the presence of aluminum chloride to form a first reaction product and then reacting the first reaction product with aqueous phosphoric acid to form the arylphosphinic acid. The arylphosphinic acid, which is insoluble in the aqueous phosphoric acid, is easily separated from the soluble salts which are also formed.

The aromatic compounds which are used in the practice of the present invention are those which are susceptible to electrophilic ring substitution, having at least one unsubstituted ring position and up to 5 non-interfering substituents. As used herein the term "non-interfering substituent" means a substituent which does not itself react with $PCl_3$ or with other substances used in or formed by the process herein to an extent that would unreasonably interfere with formation of the desired product. These aromatic compounds include, but are not limited to compounds represented by the formula:

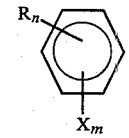

wherein each R is independently hydrogen, alkyl, alkoxy, alkylthio, aryl, substituted aryl or cycloalkyl; n represents a number ranging from 0 to 5; X represents hydrogen or a halogen and m represents a number ranging from 0 to 5. Preferred aromatic compounds are those wherein R is hydrogen, alkyl having up to about 4 carbon atoms or alkoxy having up to about 4 carbon atoms. Exemplary aromatic compounds include benzene, toluene, naphthalene, p-xylene, o-xylene, p-chlorotoluene, o-chlorotoluene, 1,2,4-trimethylbenzene, 1,3,5-trimethylbenzene, cumene, durene, and biphenyl.

Heterocyclic compounds such as thiophene can be used as the aromatic compound, and compounds having more than one benzene ring such as diphenylmethane, polystyrene and polyphenyl ethers can also be used.

A particularly preferred aromatic compound is p-xylene.

The reaction between the aromatic compound and $PCl_3$ is preferably carried out in an excess of phosphorus trichloride. The amount of phosphorus trichloride charged therefore ranges from about 1 to about 5 moles per mole of aromatic compound charged, and preferably from about 2 to about 4 moles phosphorus trichloride per mole aromatic compound.

It is also preferred to use relatively large amounts of the aluminum chloride catalyst. The amount of aluminum chloride charged therefore ranges from about 1 mole aluminum chloride per mole aromatic compound to about 5 moles aluminum chloride per mole aromatic compound, although a range of from about 1 to about 1.5 moles aluminum chloride per mole aromatic compound is preferred. The process is operable at lower or higher catalyst ratios, but with lower catalyst ratios conversion to the desired product may not be as complete as desired, while with higher ratios unwanted by-products resulting from multiple substitution on phosphorus could result.

The reaction between the aromatic compound and phosphorus trichloride is generally conducted at a temperature ranging from about 20° C. to about 100° C. or higher, although a temperature ranging from about 50° C. to about 75° C. is preferred. The subsequent reaction of the first reaction product with aqueous phosphoric acid can be conducted at room temperature or at a reduced temperature, but an elevated temperature (i.e., between about 50° C. and about 75° C.) is preferred as conversion appears to be more complete at the elevated temperatures.

The aqueous phosphoric acid which is used in the practice of the present invention is preferably at a strength of at least 10% by weight. The use of more dilute acids can lead to difficulty in keeping the aluminum salts which are formed in solution.

The amount of phosphoric acid used is important to achieving successful results, and is preferably at least 2.5 moles phosphoric acid (100% basis) per mole aluminum chloride charged.

When the first reaction product, (thought to be an aluminum complex of a phosphonous dichloride) reacts with the aqueous phosphoric acid, the arylphosphinic acid forms as an insoluble organic phase while the aluminum goes into solution as a soluble salt. The arylphosphinic acid can then be separated without encountering the difficulties caused by the aluminum chloride complexes in the prior art.

The arylphosphinic acid which is formed can be removed by standard work-up techniques. Thus, for example, the arylphosphinic acid can be extracted with methylene chloride, which can then be evaporated to produce the acid in a relatively pure state.

In order that the present invention be more fully understood, the following example is given by way of illustration. No specific details or enumerations contained therein should be construed as limitations to the present invention except insofar as they appear in the appended claims. All parts and percentages are by weight unless otherwise specifically designated.

EXAMPLE

A 250 ml. 3 neck flask equipped with thermometer and thermostat, mechanical stirrer and condenser, through which evolved gases exit to a caustic trap, was charged with 60 ml. of phosphorus trichloride (0.69 mole), 23.9 ml. of p-xylene (0.20 mole) and 34.2 g. of aluminum trichloride (0.26 mole). The mixture was stirred and heated at reflux until gas evolution ceased (2.5 hours). This product was then loaded into an addition funnel.

A one liter, 3-neck flask was fitted with a thermometer, mechanical stirrer and the loaded addition funnel and provided with a caustic scrubber for exit gases as well as a nitrogen sweep. To the flask was charged 150 g. of ice and 84 ml. of 85% phosphorus acid. The addition funnel contents were added dropwise to the stirred contents of the flask. An ice bath was periodically used to moderate the internal temperature which was not allowed to exceed 60° C. After addition was complete the contents of the flask were heated at 75° C. until gas evolution ceased. The resultant two phase mixture, after cooling, was extracted two times each with 75 ml. of methylene chloride. The organic extract was stirred with 150 ml. of water and then sodium bicarbonate was added until gas evolution ceased (42 g.). Two hundred and fifty ml. more of water was added and the aqueous layer was separated. The methylene chloride was extracted with an additional 100 ml. of water and the resultant emulsion was broken by vacuum filtration. The combined aqueous extracts, which had a pH of 8, were acidified with concentrated hydrochloric acid to pH 1 (50 g). This mixture was saturated with sodium chloride and extracted three times with 100 ml. each time of methylene chloride. The combined extracts were dried with activated Linde 3A molecular sieves and filtered. Methylene chloride was then removed in vacuo. In this manner 20 g. of 2,5-dimethylbenzenephosphinic acid (60% of theoretical yield) which was pure by 'H NMR and melted at 77°–83° C. was obtained.

I claim:

1. A process for the preparation of arylphosphinic acid comprising reacting an aromatic compound susceptible to electrophilic ring substitution with phosphorus trichloride in the presence of aluminum chloride to form a first reaction product and then reacting said first reaction product with aqueous phosphoric acid, at a strength of at least 10% by weight, to form an insoluble arylphosphinic acid and a soluble aluminum salt.

2. The process of claim 1 wherein said aromatic compound is an aromatic compound represented by the structure

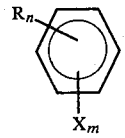

wherein each R is independently hydrogen, alkyl, alkoxy, alkylthio, aryl, substituted aryl or cycloalkyl; X represents hydrogen or a halogen, n represents a number ranging from 0 to 5 and m represents a number ranging from 0 to 5; provided that m+n is not more than 5.

3. The process of claim 2 wherein said aromatic compound is a compound selected from the group consisting of benzene, toluene, naphthalene, p-xylene, o-xylene, p-chlorotoluene, o-chlorotoluene, 1,3,5-trimethyl benzene, 1,2,4-trimethylbenzene, cumeme, durene and biphenyl.

4. The process of claim 3 wherein said aromatic compound is p-xylene.

5. The process of claim 1 wherein the amount of $PCl_3$ present during the reaction between the aromatic compound and $PCl_3$ ranges from 1 to about 5 moles $PCl_3$ per mole aromatic compound.

6. The process of claim 5 wherein the amount of aluminum chloride present during said reaction between said aromatic compound and said $PCl_3$ ranges from 1 to about 5 moles aluminum chloride per mole aromatic compound.

* * * * *